(12) United States Patent
Hamilton et al.

(10) Patent No.: US 6,516,678 B2
(45) Date of Patent: Feb. 11, 2003

(54) INDUSTRIAL DIAGNOSTIC GAUGE INDICATOR INSERT AND INDUSTRIAL DIAGNOSTIC GAUGES HAVING SAME

(76) Inventors: Michael G. Hamilton, 10134 Sagedalo, Houston, TX (US) 77089; Sam M. Ditta, 125 Woodridge, Alvin, TX (US) 77511

( * ) Notice: Subject to any disclaimer, the term of this patent is extended or adjusted under 35 U.S.C. 154(b) by 0 days.

(21) Appl. No.: 09/904,827

(22) Filed: Jul. 13, 2001

(65) Prior Publication Data

US 2002/0053236 A1 May 9, 2002

Related U.S. Application Data

(63) Continuation-in-part of application No. 09/711,112, filed on Nov. 9, 2000, now Pat. No. 6,556,518.

(51) Int. Cl.[7] .............................................. G01D 13/04
(52) U.S. Cl. ................................................... 73/866.3
(58) Field of Search ............................... 73/866.3, 499, 73/732–743, 1.57; 116/284–305, 310, DIG. 6, DIG. 35, DIG. 36; 368/228, 232, 235, 238; 359/527; 362/23, 25, 28; 374/208

(56) References Cited

U.S. PATENT DOCUMENTS

| | | | | |
|---|---|---|---|---|
| 1,755,106 A | * | 4/1930 | Eckardt | ........................ 73/740 |
| 2,627,245 A | * | 2/1953 | Kimball | ........................ 116/301 |
| 3,191,306 A | | 6/1965 | De Valrea Kierans | |
| 3,621,811 A | * | 11/1971 | Hill, Jr. | |
| 4,004,546 A | | 1/1977 | Harland | |
| 4,020,787 A | | 5/1977 | Castro et al. | |
| 4,561,042 A | | 12/1985 | Wehner | |
| 5,629,817 A | * | 5/1997 | Shiomi | ....................... 360/96.5 |
| 6,121,581 A | * | 9/2000 | Hegedus | ....................... 219/390 |

FOREIGN PATENT DOCUMENTS

| | | | |
|---|---|---|---|
| CH | 672 954 A5 | 1/1990 | |
| DE | 2512376 A1 | 9/1976 | |
| DE | 3537364 A1 | 4/1987 | |
| DE | 19520460 A1 | 1/1996 | |
| GB | 110614 | * 10/1917 | ............. 73/DIG. 6 |
| GB | 719398 | 12/1954 | |
| GB | 1507541 | 4/1978 | |

* cited by examiner

*Primary Examiner*—Robert R. Raevis
(74) *Attorney, Agent, or Firm*—Anthony F. Matheny; Andrews & Kurth L.L.P.

(57) ABSTRACT

The invention is directed to indicator inserts for industrial diagnostic gauges and to industrial diagnostic gauges having at least one indicator insert that are utilized in industrial applications such as pressure and temperature gauges utilized in petrochemical plants. The indicator insert preferably includes at least one indicator insert marking having luminescent materials and reflective materials to facilitate accurate reading of the industrial diagnostic gauges in low and no light conditions from distances greater than 4 feet. Broadly, the industrial diagnostic gauges include a housing, a diagnostic member, a face, at least one hand operatively associated with the diagnostic member, a clear window, an indicator insert, and a retaining ring. The indicator insert includes a top surface that includes at least one indicator insert marking.

12 Claims, 3 Drawing Sheets

INDUSTRIAL DIAGNOSTIC GAUGE INDICATOR INSERT AND INDUSTRIAL DIAGNOSTIC GAUGES HAVING SAME

CROSS REFERENCE TO RELATED APPLICATIONS

This application is a continuation-in-part of U.S. application Ser. No. 09/711,112, filed Nov. 9, 2000, now U.S. Pat. No. 6,556,518, issued Sep. 10, 2002.

BACKGROUND OF THE INVENTION

1. Field of the Invention

The invention is directed to indicator inserts for diagnostic gauges that are utilized in industrial applications, and in particular, to indicator inserts for diagnostic gauges utilized in industrial locations that can be viewed and read in low and no light conditions.

2. Description of Related Art

Industrial diagnostic gauges, or diagnostic gauges, are required in numerous industrial applications. Many of these applications require the diagnostic gauges to be placed in locations that are difficult for a person to access. For example, a diagnostic gauge may be located in a radioactive or other hazardous location, e.g., nuclear power plants, biohazard laboratories; disposed high above the ground, e.g., on a tower of a petrochemical plant; located in close proximity to moving parts of a machine, or any other location that restricts a person desiring to read the diagnostic gauge from safely and easily approaching the diagnostic gauge.

The necessity of a person attempting to read the diagnostic gauge to get as close as possible to the diagnostic gauge is increased during times when little or no light is present, e.g., at night, when overhead lighting, either natural, e.g., sunlight, or artificial light, is unavailable, or when the diagnostic gauges are placed in obstructed areas. Generally, a diagnostic gauge cannot be accurately read at distances greater than about four feet when little or no light is present. Under these conditions, the person must take special precautions to approach the diagnostic gauge, e.g., put on special clothing to enter radioactive areas or read the diagnostic gauges in inclement weather; or climb ladders to reach the diagnostic gauge disposed high above the ground. Further, many times locating a diagnostic gauge desired to be read in low or no light conditions is very difficult.

Prior attempts to address the problem of reading diagnostic gauges in low or no light have been directed at adding either external lighting or internal lighting to the diagnostic gauge. External lighting requires leaving overhead lights on at all times or placing additional lighting focused on the diagnostic gauge. Internal lighting requires wiring the diagnostic gauge with electrical circuitry and/or batteries, to illuminate the diagnostic dial, or face. Both of these approaches increase the cost of the diagnostic gauge and/or the construction and maintenance of the additional wiring and equipment.

Accordingly, prior to the development of the present invention, there has been no indicator insert or industrial diagnostic gauge that can be read in low or no light conditions, which: do not require the presence of an electrical light source located internally within, or externally in close proximity to, the industrial diagnostic gauge; do not substantially increase the cost of the industrial diagnostic gauge; permit the industrial diagnostic gauge to be easily located; and permit the industrial diagnostic gauge to be read from a distance. Therefore, the art has sought an indicator insert and industrial diagnostic gauge that can be read in low or no light conditions, which: do not require the presence of an electrical light source located internally within, or externally in close proximity to, the industrial diagnostic gauge; do not substantially increase the cost of the industrial diagnostic gauge; permit the industrial diagnostic gauge to be easily located; and permit the industrial diagnostic gauge to be read from a distance.

SUMMARY OF INVENTION

In accordance with the invention the foregoing advantages have been achieved through the present indicator insert comprising: a plate having an outer perimeter, a front surface, a back surface, and a thickness defined between the front surface and the back surface, the front surface including at least one indicator insert marking.

A further feature of the indicator insert is that the plate may include an opening defining an inner perimeter. Another feature of the indicator insert is that the plate may include at least one pointer disposed along the inner perimeter, each of the at least one pointers having the at least one indicator insert marking. An additional feature of the indicator insert is that the at least one indicator insert marking may include at least one reflective material. Still another feature of the indicator insert is that each of the at least one indicator insert marking may include at least one luminescent material. A further feature of the indicator insert is that each of the at least one indicator may be malleable. Another feature of the indicator insert is that each of the at least one indicator insert marking may include at least one reflective material. An additional feature of the indicator insert is that each of the at least one indicator insert marking may include at least one luminescent material. Still another feature of the indicator insert is that the plate may be transparent.

In accordance with the invention the foregoing advantages have been achieved through the present industrial diagnostic gauge comprising: a housing; a diagnostic member having a face and at least one hand operatively associated with the diagnostic member, the diagnostic member being disposed within the housing; a retaining ring; and an indicator insert disposed between the retaining ring and the face, the indicator insert having a plate, wherein the plate includes an outer perimeter, a front surface, a back surface, and a thickness defined between the front surface and the back surface, the front surface including at least one indicator insert marking.

A further feature of the industrial diagnostic gauge is that the plate may include an opening defining an inner perimeter. Another feature of the industrial diagnostic gauge is that the plate may include at least one pointer disposed along the inner perimeter, each of the at least one pointers having the at least one indicator insert marking. An additional feature of the industrial diagnostic gauge is that each of the at least one indicator insert marking may include at least one reflective material. Still another feature of the industrial diagnostic gauge is that each of the at least one indicator insert marking may include at least one luminescent material. A further feature of the industrial diagnostic gauge is that each of the at least one indicator may be malleable. Another feature of the industrial diagnostic gauge is that each of the at least one indicator insert marking may include at least one reflective material. An additional feature of the industrial diagnostic gauge is that each of the at least one indicator insert marking may include at least one luminescent material. Still another feature of the industrial diagnostic gauge is that the at least one hand may include at least one reflective material. A further feature of the industrial diagnostic gauge is that the at least one hand may include at least one luminescent material. Another feature of the industrial diagnostic gauge is that the plate may be transparent.

The indicator insert and industrial diagnostic gauge that can be read in low or no light conditions have the advantages of: not requiring the presence of an electrical light source located internally within, or externally in close proximity to, the industrial diagnostic gauge; not substantially increasing the cost of the industrial diagnostic gauge; permitting the industrial diagnostic gauge to be easily located; and permitting the industrial diagnostic gauge to be read from a distance.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION AND SPECIFIC EMBODIMENTS

The present invention relates to indicator inserts and industrial diagnostic gauges, or diagnostic gauges, that can be read under low, or no light conditions, and can be read at distances up to at least 10 feet. Diagnostic gauges are herein defined as pressure gauges, differential gauges, bi-metal thermometers, glass industrial thermometers, surface thermometers, gas actuated thermometers, vapor tension thermometers, level gauges, or any other diagnostic gauge utilized in industrial applications. Indicator inserts are devices that may be included as part of diagnostic gauges to facilitate reading the diagnostic gauge in low light and no light conditions.

Figure 2:
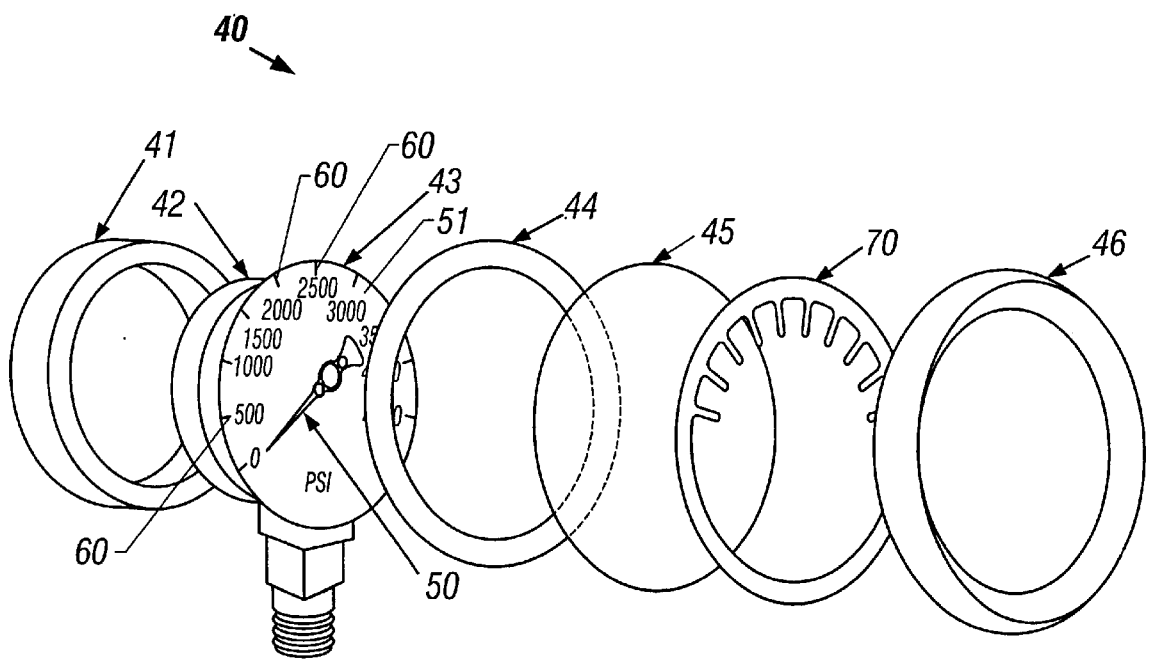
FIG. 2 is an exploded perspective view of an industrial diagnostic gauge having the indicator insert shown in FIG. 1.
Figure 3:
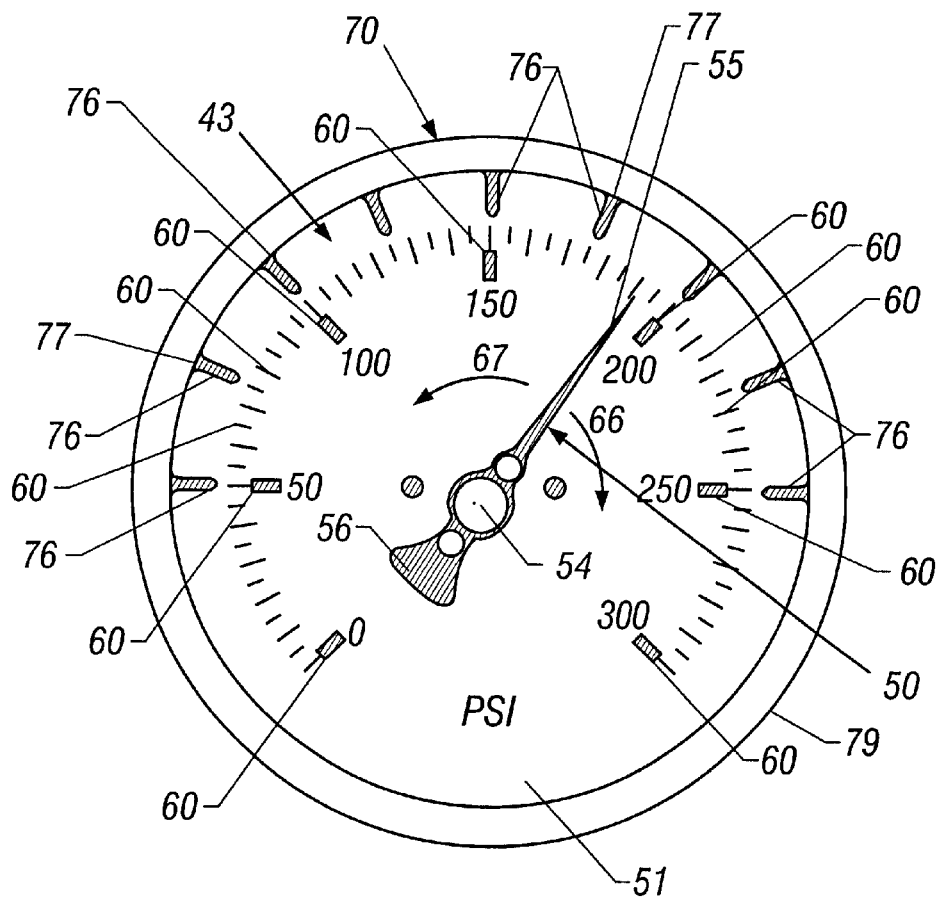
FIG. 3 is a front view of the industrial diagnostic gauge shown in FIG. 2.
Figure 4:
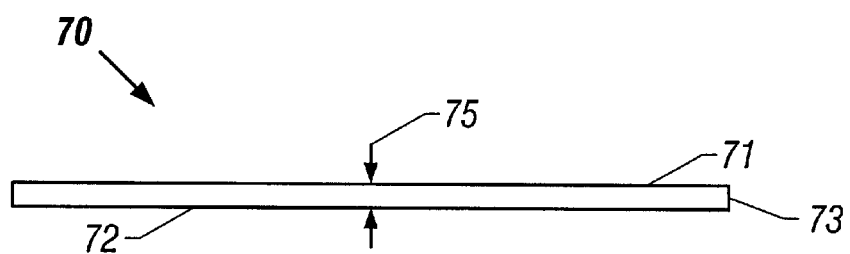
FIG. 4 is a side view of the indicator insert shown in FIG. 1.
Figure 5:
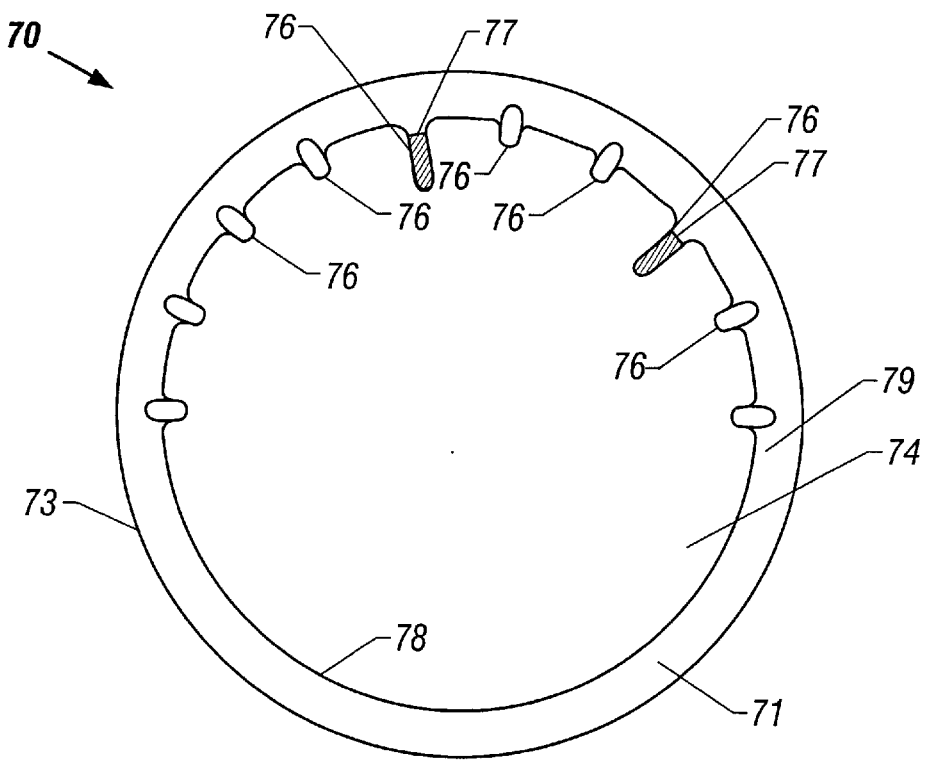
FIG. 5 is a front view of the indicator insert shown in FIG. 1 modified for indicating one range of measurements.

Referring now to FIGS. 1–5, indicator insert 70 includes plate 79 having front surface 71, back surface 72, and outer perimeter 73. Front surface 71 and back surface 72 define thickness 75 therebetween (FIG. 4). In a preferred embodiment, indicator insert 70 includes opening 74 defining inner perimeter 78 (FIGS. 1–3 and 5). Inner perimeter 78 includes at least one indicator, or pointer, 76. As shown in FIGS. 1–3 and 5, each of the at least one pointers 76 include at least one indicator insert marking 77. It is to be understood, however, that one or more of the indicators 76 may not include at least one indicator insert marking 77. Indicator insert markings 77 facilitate quick and easy reading of the diagnostic gauge 40 by permitting a person to determine the location of hand 50 relative to indicator insert markings 77.

While indicator insert 70 and pointer 76 may be formed out of any material desired or necessary to accurately indicate the quantitative measurement of diagnostic gauge 40, pointer 76 is preferably formed out of a malleable material, e.g., aluminum or stainless steel. Accordingly, each pointer 76 may be bent as desired or necessary so that indicator insert 70 indicates a single range (FIG. 5), or so that only one pointer 76 is utilized (not shown).

Referring now to FIG. 2, indicator insert 70 is included as part of industrial diagnostic gauge 40. In addition to indicator insert 70, industrial diagnostic gauge 40 also includes housing 41, diagnostic member 42, face 43, and at least on needle, or hand, 50. Face 43 includes a top surface 51.

Hand 50 is operatively associated with diagnostic member 42. Accordingly, as diagnostic member 42 is activated, e.g., the pressure or temperature increases or decreases, the at least one hand 50 moves, or points, to quantitatively indicate the level of whatever the industrial diagnostic gauge is designed to measure, e.g., the pressure or temperature. Preferably, the at least one hand 50 points relative to at least one face marking 60 disposed on face 43. In the embodiment shown in FIGS. 1 and 2, hand 50 is permitted to move in a clockwise direction (arrow 66) and a counter-clockwise direction (arrow 67).

Industrial diagnostic gauge 40 also preferably includes gasket 44, clear window 45, and retaining ring 46. Housing 41, diagnostic member 42, face 43, gasket 44, clear window 45, retaining ring 46, and indicator insert 70 may be any shape and manufactured out of any material desired or necessary depending upon the application in which the diagnostic gauge 40 will be utilized. As shown in FIGS. 2 and 3, diagnostic member 42 measures pressure. Therefore, diagnostic gauge 40 shown in FIGS. 2 and 3 is a pressure gauge. It is to be understood that diagnostic member 42 may be any industrial diagnostic device known to persons of ordinary skill in the art. For example, diagnostic member 42 may measure temperature. In these embodiments, the diagnostic gauge 40 is a temperature gauge.

As mentioned above, disposed along top surface 51 of face 43 is preferably at least one face marking 60. As shown in FIGS. 2 and 3, numerous face markings 60 are disposed along the perimeter of face 43. Preferably, face markings 60 are incremental. In other words, each face marking 60 represents a specific, and identical, increase or decrease in the reading provided by the diagnostic member 42, e.g., 10 degrees or 5 psi (FIG. 2). Face markings 60 may be printed on, or affixed to, face 43 using any method or device known to persons skilled in the art. In one embodiment, face markings 60 are formed using paint. In another embodiment, markings 60 are formed using stickers. In still another embodiment, markings 60 are formed using luminescent materials that glow, or illuminate, without the presence of external or internal light sources. While numerous luminescent materials are contemplated to be acceptable, one suitable luminescent material is NIGHTLIGHT20™, a phosphorescent powder sold by DORAK International Corporation. In this embodiment, direct light or ambient light charges, or energizes, the luminescent material which then glows or illuminates in low light and no light conditions permitting a person to read the markings at distances of at least about 10 feet without assistance from internal or external lighting.

In one specific embodiment, face markings 60 are formed using reflective materials that are capable of reflecting substantially all light that shines onto the reflective materials. Examples include reflective paint, stickers, tape, or other reflective adhesives such as vinyl reflective strips made and sold by 3M Corporation. In this embodiment, the reflective materials permit a person to accurately read the markings at distances up to about 50 feet or more in low or no light conditions when the person shines a light, e.g., a flashlight, on the markings 60.

As mentioned above, face 43 may be constructed out of any material desired or necessary depending upon the application in which the diagnostic gauge 40 will be utilized. In one embodiment, top surface 51 may include reflective materials as discussed above. In another embodiment, face 43 includes a luminescent material evenly distributed along top surface 51 of face 43. Alternatively, the luminescent material may be incorporated into the material used to form the top surface 51 of face 43. For example, face 43, and top surface 51, may be manufactured using a plastic extrusion process in which the luminescent material is incorporated into the plastic prior to extruding the plastic into the shape of face 43. In one embodiment, top surface 51 of face 43 is coated with a luminescent paint that is formed by combining NIGHTLIGHT20™ luminescent powder with clear acrylic paint. The luminescent paint is distributed evenly along top surface 51 by any method known to persons skilled in the art, e.g., spraying, or dipping, face 43 with, or into, the luminescent paint. In one embodiment, two parts luminescent powder combined with five parts clear acrylic paint has been found to provide the desired results. As mentioned above, the luminescent material permits a person to read the industrial diagnostic gauge from distances of at least about 10 feet without assistance from internal or external light sources. Additionally, the luminescent material permits a person to determine the location of an industrial diagnostic gauge 40 in low or no light conditions from distances up to about 100 feet away. This feature is beneficial in large industrial plants having numerous industrial diagnostic gauges located throughout the plant at varying levels.

Hand 50 may also include at least one luminescent material and/or at least one reflective material. Hand 50 is operatively associated with diagnostic member 42 at connection 54 which permits hand 50 to move as discussed above. In one embodiment, hand 50 includes two ends, an indicator end 55 and a balance end 56, disposed opposite of each other relative to connection 54. Indicator end 55 is used to read the diagnostic gauge 40. In one embodiment, indicator end 55 aligns with, or in close proximity with, at least one face marking 60 and/or one indicator insert marking 77. Balance end 56 may offset the weight of indicator end 55, and thus, provide balance to hand 50. Alternatively, balance end 56 may be operatively associated with diagnostic member 42, i.e., connection 54 is located at balance end 56. In one embodiment, only indicator end 55 of hand 50 includes the at least one luminescent material and/or at least one reflective material. In a preferred embodiment, the indicator end 55 of hand 50 includes at least one reflective material, thereby permitting the position of indicator end 55 of hand 50 to be easily determined by shining light, e.g., from a flashlight, on the indicator end 55. Accordingly, industrial diagnostic gauge 40 may be accurately read, from varying distances.

In one specific embodiment, industrial diagnostic gauge 40 includes a face 43 having at least one hand 50 having at least one reflective material, and indicator insert 70 having at least one indicator insert marking 77. In this embodiment, hand 50 contrasts sharply with the at least one indicator insert marking 77. Accordingly, industrial diagnostic gauge 40 may be easily located, and accurately read, by a person. Further, after the diagnostic gauge 40 is manufactured, no additional maintenance to indicator insert makings 77 or hand 50 is required. Moreover, no additional wiring is required assist a person to accurately read the industrial diagnostic gauge 40.

Figure 1:
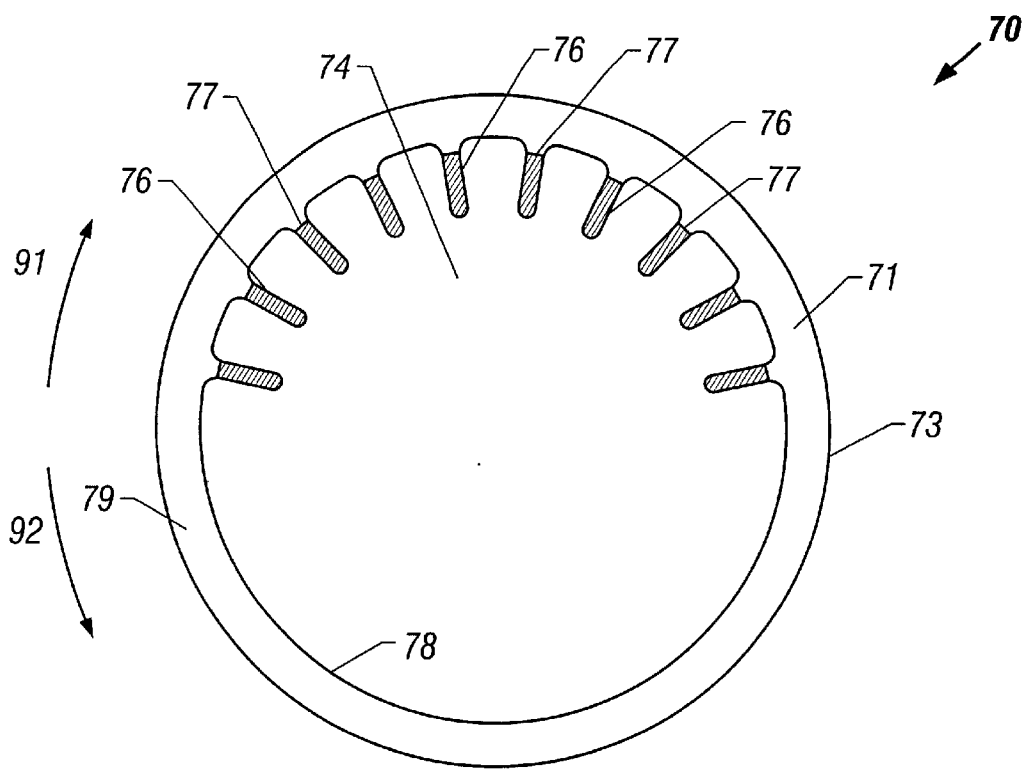
FIG. 1 is a front view of an indicator insert of the present invention.
Figure 6:
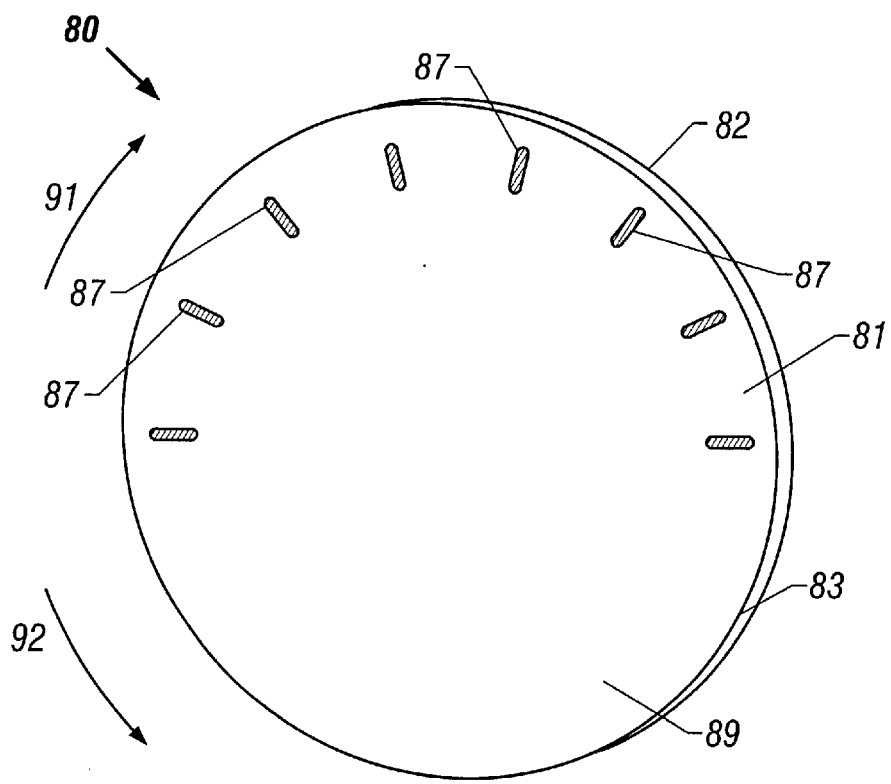
FIG. 6 is a front view of another indicator insert of the present invention.

Another benefit of indicator insert 70 is that it is adjustable. As discussed above, pointer 76 is preferably formed out of a malleable material to permit each pointer 76 to be bent, thereby customizing indicator insert 70 to indicate desired readings or ranges. Additionally, indicator insert 70 may be rotatable in the direction of arrows 91 and 92 (FIGS. 1 and 6). Accordingly, indicator insert 70 maybe placed in alignment with face markings 60 or other desired quantitative measurement indicators or markings.

The indicator inserts 70 of the present invention may be manufactured by applying at least one indicator insert marking 77 to top surface 51. Indicator insert 70 may then be disposed within housing 41. As shown in FIG. 2, indicator insert 70 is disposed on top surface 51 of face 43, e.g., between clear window 45 and retaining ring 46. Retaining ring 46 is then connected to housing 41 using any method or device known to persons skilled in the art, e.g., screws, bolts, threaded connectors, etc., to capture diagnostic member 42, clear window 45, and indicator insert 70 between housing 41 and retaining ring 46. Water or other liquid (not shown) may also be disposed between face 43 of diagnostic member 42 and clear window 45.

It is to be understood that indicator insert 70 may be tightly captured between retaining ring 46 and clear window 45 such that indicator insert 70 is not rotatable. Alternatively, retaining ring 46 may not be secured so tightly to housing 41, thereby permitting indicator insert 70 to be rotatable. Further, retaining ring 46 may be easily modified to tightly secure clear window 45 and retaining ring 46 to housing 41, and include a groove (not shown) that captures indicator insert 70 and permits indicator insert 70 to be rotatable.

Luminescent material may be applied to one or more indicator insert markings 77. Alternatively, reflective material may be applied to one or more indicator insert markings 77. In one specific embodiment, luminescent material is applied to face 43 and reflective material is applied to hand 50 and to indicator insert markings 77. In another specific embodiment, reflective material is applied to hand 50 and to indicator insert markings 77. The luminescent material and the reflective material may be applied to indicator insert markings 77, face 43, or hand 50 in any manner known to persons skilled in the art of applying these materials. For example, the luminescent material and the reflective material may be applied to indicator insert markings 77, face 43, or hand 50 as discussed in greater detail above.

Referring now to FIG. 6, in another specific embodiment, indicator insert 80 includes plate 89 having front surface 81, back surface 82, and outer perimeter 83. Thickness (not shown) is defined by front surface 81 and back surface 82 in the same manner as described above regarding the embodiment shown in FIGS. 1–4 (thickness 75). At least one indicator insert marking 87 is disposed along top surface 81; and preferably, a plurality of indicator insert markings 87 are disposed along top surface 81 to correspond with the quantitative increments, e.g., face markings 60 on face 43 of diagnostic gauge 40. While plate 89 may be formed out of any material, preferably plate 89 is transparent and is formed out of plastic, e.g., clear polypropylene.

Like the embodiment shown in FIGS. 1–5, indicator insert 80 (FIG. 6) is adjustable by rotating indicator insert 80 in the directions of arrows 91, 92. Accordingly, indicator insert markings 87 may be aligned with face markings 60 or other desired quantitative measurement indicators or markings.

As is readily ascertainable by persons of ordinary skill in the art, the embodiment shown in FIG. 6 does not include an opening, an inner perimeter, or at least one pointer. Instead, indicator insert markings 87 are placed on top surface 81 of indicator insert 80.

It is to be understood that the invention is not limited to the exact details of construction, operation, exact materials, or embodiments shown and described, as obvious modifications and equivalents will be apparent to one skilled in the art. For example, the diagnostic gauge may include reflective materials associated only with one of either the hand, face marking, face, or indicator insert. Alternatively, the diagnostic gauge may include luminescent materials associated only with one of either the face, hand, face marking, or indicator insert. In another embodiment, the luminescent materials and the reflective materials may be associated with the face, hand, face marking, and indicator insert in any other combination that facilitates accurate reading of the industrial diagnostic gauge in low or no light conditions from varying distances. In still another embodiment, hand may move in a horizontal or a vertical direction. Accordingly, the invention is therefore to be limited only by the scope of the appended claims.

What is claimed:

1. An indicator insert comprising:
    a plate having an outer perimeter, a front surface, a back surface, and a thickness defined between the front surface and the back surface, the front surface including at least one indicator insert marking, at least one of the at least one indicator insert markings having at least one reflective material.

2. The indicator insert of claim 1, wherein the plate includes an opening defining an inner perimeter.

3. The indicator insert of claim 2, wherein the plate includes at least one pointer disposed along the inner perimeter, wherein at least one pointer includes the at least one indicator insert marking.

4. The indicator insert of claim 3, wherein each of the at least one indicator insert markings includes at least one reflective material.

5. The indicator insert of claim 3, wherein each of the at least one pointer is malleable.

6. The indicator insert of claim 5, wherein each of the at least one indicator insert markings includes at least one reflective material.

7. An industrial diagnostic gauge comprising:
    a housing;
    a diagnostic member having a face and at least one hand operatively associated with the diagnostic member, the diagnostic member being disposed within the housing;
    a retaining ring; and
    an indicator insert disposed between the retaining ring and the face, the indicator insert having a plate, wherein the plate includes an outer perimeter, a front surface, a back surface, and a thickness defined between the front surface and the back surface, the front surface including at least one indicator insert marking, at least one of the at least one indicator insert markings having at least one reflective material.

8. The indicator insert of claim 7, wherein the plate includes an opening defining an inner perimeter.

9. The indicator insert of claim 8, wherein the plate includes at least one pointer disposed along the inner perimeter, wherein at least one pointer includes the at least one indicator insert marking.

10. The indicator insert of claim 9, wherein each of the at least one indicator insert markings includes at least one reflective material.

11. The indicator insert of claim 9, wherein each of the at least one pointer is malleable.

12. The indicator insert of claim 11, wherein each of the at least one indicator insert markings includes at least one reflective material.

* * * * *